United States Patent [19]

Inskip

[11] Patent Number: 4,551,551

[45] Date of Patent: Nov. 5, 1985

[54] PREPARATION OF BIS(AMINOPHENYL) ETHERS FROM (N-ACETYL)AMINOPHENOLS OR THEIR PHENOLATES

[75] Inventor: Ervin B. Inskip, Troy, Ill.

[73] Assignee: Mallinckrodt, Inc., St. Louis, Mo.

[21] Appl. No.: 424,134

[22] Filed: Sep. 27, 1982

[51] Int. Cl.[4] .............................................. C07C 85/00
[52] U.S. Cl. .................................... 564/430; 564/221; 564/420; 564/423
[58] Field of Search .................... 564/221, 430, 423

[56] References Cited

U.S. PATENT DOCUMENTS

| | | | |
|---|---|---|---|
| 1,900,442 | 3/1933 | Grether | 564/221 X |
| 3,189,647 | 6/1965 | Syman | 260/558 |
| 3,192,263 | 6/1965 | Spiegler | 260/571 |
| 3,277,175 | 10/1966 | Clemens, Jr. | 260/576 |
| 3,634,519 | 1/1972 | Bentz et al. | 260/612 R |
| 3,654,364 | 4/1972 | Meckel et al. | 260/571 |

FOREIGN PATENT DOCUMENTS

| | | | |
|---|---|---|---|
| 0992991 | 7/1976 | Canada | 564/430 |
| 1560940 | 3/1969 | France . | |
| 0449660 | 6/1969 | Japan | 564/221 |
| 1334659 | 10/1973 | United Kingdom . | |

OTHER PUBLICATIONS

Ser. No. 376,478 Merrell and Ellis filed 5-10-1982.
Ikawa, *Chemical Abstracts,* vol. 53, 21761h-21762c, (1959), "XI, Syntheses of Nitro Amino Diphenyl Ether Derivatives, 2".
Itatani et al., *Chemical Abstracts,* vol. 87, pp. 483-484, 87: 39093d, (1977), "4,4'-Diaminophenyl Ether".
Shamis et al., *Chemical Abstracts,* vol 67, p. 10206, Item 108357u, (1967), "Synthesis of 4,4'-Diaminodiphenyl Ether".

*Primary Examiner*—Paul F. Shaver
*Attorney, Agent, or Firm*—R. G. Jackson; R. J. Klostermann; L. N. Goodwin

[57] ABSTRACT

Bis(aminophenyl) ethers are prepared by effecting condensation reaction of an (N-acetyl)aminophenol or the corresponding sodium or potassium (N-acetyl)aminophenate with a halonitrobenzene under condensation reaction conditions to form an (N-acetyl)aminophenylnitrophenyl ether and hydrogenating the nitro group thereof under nitro- group hydrogenation conditions to form an (N-acetyl)bis(aminophenyl) ether. The latter compound is hydrolyzed with aqueous mineral acid under acid hydrolysis conditions to form an acidic aqueous dispersion of the bis(aminophenyl) ether product, which can readily be recovered from the disperson. Final bis(aminophenyl) ether products thus prepared are typically of high purity and excellent color properties, i.e., substantially colorless.

16 Claims, No Drawings

PREPARATION OF BIS(AMINOPHENYL) ETHERS FROM (N-ACETYL)AMINOPHENOLS OR THEIR PHENOLATES

BACKGROUND OF THE INVENTION

This invention relates to preparation of diaminodiphenyl ethers, and more particularly to preparation of bis(aminophenyl)ethers (e.g. oxydianiline) from N-acetylaminophenol compounds.

Bis(aminophenyl)ethers (hereinafter sometimes referred to collectively as BAPE's) are known to be valuable as bifunctional cross-linking and network-extending agents for polymeric resins, plastics and elastomers. There is a substantial demand by users of BAPE's for high-purity and substantially colorless commercial grade of BAPE products, especially such ODA products.

In Canadian Pat. No. 992,991 (incorporated herein by reference), Jamieson et al. described and claim inter alia a process for preparing 4,4'-diaminodiphenyl ether (also known as 4,4'-oxydianiline or simply 4,4'-ODA) which comprises refluxing a mixture containing approximately equimolar amounts of p-aminophenol (sometimes referred to as PAP), p-chloronitrobenzene, and potassium carbonate in dimethylformamide, hydrogenating the resulting mixture in the presence of a catalyst, recovering the dimethylformamide (or DMF as it is commonly referred to) by distillation, and crystallizing 4,4'-diaminodiphenyl ether (i.e., 4,4'-ODA) from the residue. As described in Example 1 of the Canadian Patent, the residue (remaining after distilling to recover 80% of the DMF) was drowned with water, filtered and reprecipitated to give crude 4,4'-oxydianiline(4,4'-ODA). Example 3 of Jamieson et al. states that, after "cooling and removal of catalyst by filtration, 4,4'-ODA was isolated as a pink solid by drowning the reaction mixture, including the DMF, with water and filtering," the *pink* solid having melting point (m.p.) of 187°-189° C. In Example 4 Jamieson et al. teach that the 4,4'-ODA "was isolated in the usual way," excess p-aminophenol was removed, the resulting "light pink product" had "m.p. 188°-190° C.," and "reprecipitation from n-butanol gave a nearly colorless product, m.p. 190°-191° C."

Although the Jamieson et al. process for preparing 4,4'-ODA represents a substantial advance, there remains a substantial need in the art for an improved process for preparing 4,4'-ODA (and other bis(aminophenyl)ethers). There also remains a need for an improved process for making high purity substantially colorless BAPE's, especially ODA.

DESCRIPTION OF THE INVENTION

It has now been found that high purity substantially colorless BAPE's, including ODA, can be prepared in a simple and efficient manner by a new improved process which includes initially reacting an (N-acetyl)aminophenol or a corresponding (N-acetyl)aminophenate with a halonitrobenzene.

Generally stated, the present invention provides in a first aspect thereof a process for preparing a high-purity substantially colorless bis(aminophenyl)ether product which comprises (a) effecting condensation reaction of a sodium or potassium (N-acetyl)aminophenate with a halonitrobenzene under condensation reaction conditions to form an (N-acetyl)aminophenylnitrophenyl ether, (b) hydrogenating the nitro group of said ether under nitro-group hydrogenation reduction conditions to form an (N-acetyl)bis(aminophenyl)ether, (c) hydrolyzing the (N-acetyl)bis(aminophenyl)ether with aqueous mineral acid under acid hydrolysis conditions to form an acidic aqueous dispersion of the bis(aminophenyl)ether product, and (d) recovering said bis-(aminophenyl)ether product from said dispersion.

In a second aspect, generally stated, this invention also provides a process for preparing a high-purity 4,4'-oxydianiline product which comprises (a) refluxing a mixture comprising approximately equimolar amounts of (i) (N-acetyl)p-aminophenol, (ii) a halonitrobenzene, and (iii) potassium or sodium carbonate in a liquid medium comprising a dipolar aprotic solvent, thereby forming N-acetyl-4-aminophenyl-4'-nitrophenyl ether, (b) hydrogenating the nitro group of the ether compound under nitro-group hydrogenation-reduction conditions in the presence of a catalyst to form N-acetyl-bis(p-aminophenyl)ether, (c) hydrolyzing as set forth above, and (d) recovering the 4,4'-oxydianiline product from the dispersion.

The present invention provides improvements over prior processes of the type described in the Canadian patent referenced above.

DETAILED DESCRIPTION OF THE INVENTION AND OF THE MANNER AND PROCESS OF MAKING AND USING IT

In the first step of the process of this invention for preparing high-purity substantially colorless bis(aminophenyl)ether products, the condensation reaction between halonitrobenzene and sodium or potassium (N-acetyl)aminophenate may be effected under any suitable condensation reaction conditions to form an (N-acetyl)aminophenylnitrophenyl ether. The condensation reaction is preferably carried out under at least substantially anhydrous conditions in a dipolar aprotic organic solvent, which may be, for example, dimethylformamide, dimethylacetamide, mixtures thereof or the like. Dimethylformamide and anhydrous conditions are preferred. An inert atmosphere such as nitrogen (preferred), argon or the like is preferably employed. The halonitrobenzene reactant may be employed in any suitable amount, for example, from about 1.0 mole to about 1.5 moles, preferably about 1.01 to about 1.1 moles, per mole of the (N-acetyl)aminophenate. Any suitable initial concentration of the (N-acetyl)aminophenate may be employed, for example, from about 0.1 mole or less to about 10 moles or more per liter of the solvent, and preferably from about 1 mole to about 5 moles per liter.

The N-acetylated amino group of the aminophenate reactant may be in the ortho, meta or para position relative to the phenylic oxygen, and preferably is in the para position. The halogen atom of the halonitrobenzene reactant may be in the ortho, meta or para position relative to the nitro group, preferably the para position, and may be, for example, chlorine or bromine.

The preferred reactants are potassium N-acetyl-p-aminophenate and p-chloronitrobenze.

The condensation reaction can be carried out at any suitable temperature under any suitable pressure for a time sufficient to form the N-acetyl-aminophenylnitrophenyl ether. The reaction may advantageously be carried out at a reaction temperature from about 50° C. to about 250° C., preferably from about 100° C. to about 200° C., and more preferably about 140° C. to about 160° C., under approximately atmospheric pressure.

Conveniently, the condensation may be carried out under atmospheric pressure with heating at the atmospheric reflux temperature of the reaction mixture.

The time for completion of the condensation reaction is dependent on the reaction conditions employed, primarily the temperature and concentrations of the reactants. In general, the condensation is substantially completed in from about 1 hour to about 10 hours. The reaction time required for a given yield decreases with increasing temperature and reactant concentration.

In a preferred embodiment, the N-acetylaminophenate can be formed in situ in the course of, and in the reaction mixture employed for, the condensation reaction. In this embodiment, an N-acetylaminophenol and a potassium or sodium salt of a weak acid such as carbonic acid are substituted for the N-acetylaminophenate in the starting condensation reaction mixture. Suitable salts include, for example, potassium and sodium carbonate. Potassium carbonate is preferred. The initial concentration of each of the N-acetylaminophenol and potassium salt may be the same as that set forth above for N-acetylaminophenate. The N-acetylaminophenol, the potassium or sodium salt, and the halonitrobenzene may be employed in approximately equimolar or other suitable amounts, for example, from about 1.0 to 1.5 moles, preferably from about 1.01 to about 1.1 moles, of salt per mole of N-acetylaminophenol, and from about 1.0 to about 1.5 moles, preferably from about 1.02 to about 1.1 moles of halonitrobenzene per mole of N-acetylaminophenol. The above description of other reaction conditions applies to this embodiment. The preferred reactants in the preferred embodiment are N-acetyl-para-aminophenol, potassium carbonate, and para-chloronitrobenzene.

The reaction product of the condensation reaction is principally an N-acetylaminophenyl-nitrophenyl ether having the formula:

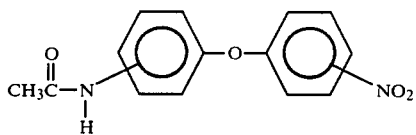

(Formula I)

wherein the N-acetylamino group and the nitro group are independently in the ortho, meta or para position (relative to the ether oxygen atom) on their respective benzene rings. The position of each such group in the ether of Formula I is the same as its position on the corresponding reactant. For example, where an orthohalonitrobenzene is employed the nitro group in the compound of Formula I is in the ortho position relative to the ether oxygen atom, and where N-acetyl-para-aminophenol (or a corresponding N-acetyl-para-aminophenate salt) is employed the N-acetylamino group is in the para position relative to the ether oxygen atom.

The compounds of Formula I above are new and useful as intermediate products in the process of this invention. A preferred compound of Formula I is N-acetyl-4-aminophenyl-4'-nitrophenyl ether. The compounds may be recovered from the reaction mixture by precipitation with water, followed by filtration, washing (e.g., with water) and drying. The intermediate product contains essentially no dimethylaminonitrobenzene.

After the condensation step is completed, hydrogenation of the nitro group of the intermediate product is effected to form an N-acetyl-diaminodiphenyl ether having the N-acetylamino group on one of the benzene rings and an unsubstituted amino group on the other benzene ring. The hydrogenation step may be carried out without recovering the intermediate product of Formula I. That is, hydrogenation may be effected directly in the condensation reaction mixture.

Preferably, however, the condensation or intermediate product is initially recovered and dispersed in an aliphatic alcoholic solvent therefor, preferably methanol, along with a hydrogenation effective amount of a hydrogenation catalyst such as supported platinum or palladium. Hydrogenation is thereafter effected, preferably in an autoclave or other high-pressure closed reaction vessel to which the solvent dispersion is added and the vessel filled with hydrogen. The dispersion is heated to an elevated temperature, for example, 90° C.–100° C., with stirring until hydrogen absorption has been effected to substantially the stoichiometric amount. The resulting product is principally the N-acetyl-diaminodiphenyl ether described above and having the formula:

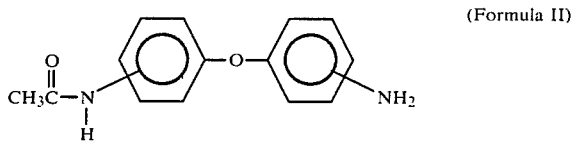

(Formula II)

The compounds of Formula II above are new and useful as intermediate products in the process of this invention. A preferred compound of Formula II is N-acetyl-4,4'-diaminodiphenyl ether.

If prior to the hydrogenation step the intermediate product of Formula I was not separated from the dimethylformamide or other aprotic solvent present in the condensation-reaction mixture, separation of the intermediate product of Formula II from such solvent is next effected. Such separation may be effected in any suitable manner, for example, by distillation removal of the solvent or, preferably, recovery of the product of Formula II by addition of a precipitating agent therefor, e.g., water, followed by filtration of the reaction mixture and washing (e.g., with water) and drying the residue.

At this stage of the process, the intermediate product of Formula II is at least substantially free of the condensation solvent, and is either in the form of a recovered solid or a dispersion in the alcoholic hydrogenation solvent. In either form, this intermediate is next hydrolyzed by effecting reaction thereof with water under acidic hydrolysis conditions to form an acidic aqueous disperson of the bis(aminophenyl)ether product being prepared. Any suitable acid may be employed for the hydrolysis.

Suitable acids include, for example, mineral acids such as hydrochloric acid, hydrobromic acid, sulfuric acid, phosphoric acid, and the like. Hydrochloric acid is preferred.

Where the intermediate of Formula II is recovered prior to hydrolysis, the hydrolysis step may be carried out by initially admixing such intermediate with the aqueous acid employed to form a hydrolysis mixture. Where the intermediate of Formula II is not so recovered, the reaction mixture containing such intermediate in the alcoholic solvent is initially admixed with the aqueous acid to form the hydrolysis mixture. The acid may be employed in any suitable amount, for example, in an amount corresponding to a molar ratio of from about 1 to about 3 moles, preferably from about 1.1 to about 1.5 moles, of the acid per mole of the N-acetylaminophenate or N-acetylaminophenol starting material.

The hydrolysis mixture may then be refluxed at any suitable pressure, e.g., one atmosphere. The hydrolysis reaction is ordinarily complete within a reflux period of from about 1 hour to about 5 hours at atmospheric pressure and a reflux temperature of about 110° C.

After completion of the hydrolysis, the hydrolyzed mixture is cooled to a suitably low temperature, for example, from about 15° C. to about 50° C., preferably about 25° C. Next the pH of the hydrolyzed mixture is adjusted upwardly to a suitable pH, for example, to from about 3 pH to about 10 pH to effect formation of the free bis(aminophenyl)ether being prepared as a readily recoverable precipitate. Such adjustment can be effected by adding an effective amount of a basic pH adjusting agent, for example, ammoniacal nitrogen and preferably aqueous ammonium hydroxide.

Where the condensation reactants are N-acetyl-para-aminophenol (or a corresponding N-acetyl-para-aminophenate salt) and a para-halonitrobenzene, the final product is 4,4'-oxydianiline(4,4'-ODA).

The pH adjusting agent employed in the pH adjustment step may be added to the reaction mixture at any suitable time, for example, after the hydrolysis step and during or after the cooling step.

For further enhancement of the quality (including purity and color) of the ODA or other BAPE products, the process of this invention preferably further includes removing residual impurities from the given product by washing same with a washing agent, which may be water. For further enhancement of product quality the process of this invention, optionally, but preferably, further includes contacting the reaction mixture with activated carbon (e.g., activated charcoal) during the hydrolysis step. Activated charcoal is preferably included when this optional contacting treatment is employed.

The activated carbon may be employed in any effective amount, for example, from about 0.1 to about 10% by weight, preferably from about 1 to about 5% by weight, and more preferably from about 1 to about 2% by weight, based on the weight of the hydrogenated precursor of the bis(aminophenyl)ether being formed.

The precipitate (i.e., ODA or other BAPE product) may be separated from the reaction mixture using known separation or recovery methods, e.g., filtration, centrifuging, and the like. If desired, the separated product may be dried under any suitable drying conditions, e.g., drying in air at a temperature up to 105° C. or higher.

Washing is carried out, if employed, following recovery of the precipitated bis(aminophenol) product from the reaction mixture.

Final ODA and other BAPE products prepared by the process of this invention have been found to contain above 98% of the BAPE per se and to be of excellent color properties.

The following non-limiting examples are given by way of illustrating the invention.

EXAMPLE 1

A stirred mixture of 75.6 g (0.5 mole) of N-acetyl-p-aminophenol (Mallinckrodt, Inc., St. Louis, Mo.), 71.1 g (0.52 mole) of anhydrous potassium carbonate, 81.0 g. (0.51 mole) of p-chloronitrobenzene and 150 ml of dimethylformamide was blanketed with nitrogen at 10 psia and heated at 150°–155° C. for 4 hours. After cooling the mixture to 120° C., 500 ml of water was added slowly while maintaining that pressure to precipitate 4-(N-acetyl)aminophenyl-4'-nitrophenyl ether, which was then collected by filtration and washed thoroughly with water. The washed precipitate and 5 g. of 5% Pd/C catalyst were added to 500 ml of methanol with stirring and heating to 100° C. in an autoclave. The resulting mixture was hydrogenated by adding a molar excess of molecular hydrogen supplied at 100 psia with continued stirring until hydrogen absorption substantially stopped. After cooling the hydrogenated mixture and removing the suspended catalyst by filtration, one liter of water was added to precipitate 4-(N-acetyl)aminophenyl-4'-aminophenyl ether (i.e., N-acetyl-4,4'-ODA), which was collected and washed thoroughly with water.

The washed N-acetyl-4,4'-ODA precipitate was dissolved in 600 ml of aqueous hydrochloric acid containing approximately 6% HCl and heated to reflux for 3 hours, thereby forming an acidic solution of 4,4'-oxydianiline. After cooling to 25° C., a crude 4,4'-oxydianiline product was precipitated from solution by adding 100 ml of aqueous 24% NH$_3$. The product was separated from the neutralized reaction mixture (8 pH) by filtration on No. 4 filter paper and thereafter washed with water till the filtrate was free of chloride ion. After drying the washed product in air at 110° C. for 4 hours, the yield was 90 g (90%) of slightly off-white 4,4'-oxydianiline (4,4'ODA).

The color of a 1% solution of the 4,4'-ODA product in dimethylformamide at 450 nm in 2-cm cells was found to be 50%T.

EXAMPLE 2

The procedure of Example 1 was repeated except carbon treatment was employed by including 5 grams of activated charcoal in the HCl-modified reaction mixture prior to precipitation with ammonia. The yield of 4,4'-ODA was found to be 90% and the color was found to be 90%T.

All the reactants and other materials for use in this invention are readily available commercial products.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A process for preparing a high-purity substantially colorless bis(aminophenyl)ether product which comprises (a) effecting condensation reaction of an (N- acetyl)aminophenol or the corresponding (N-acetyl)aminophenate with a halonitrobenzene under condensation reaction conditions to form an (N-acetyl)aminophenyl nitrophenyl ether, said conditions comprising refluxing a liquid reaction mixture comprising (i) a dipolar aprotic solvent, (ii) said (N-acetyl)aminophenol or said (N-acetyl)aminophenate, and (iii) said halonitrobenzene, (b) separating said (N-acetyl)aminophenyl nitrophenyl ether from said liquid reaction mixture and forming a dispersion of the last-mentioned ether in a lower aliphatic alcoholic solvent therefor, (c) hydrogenating the nitro group of said ether in said dispersion under nitro-group hydrogenation conditions to form an (N-acetyl)-bis-(aminophenyl)ether, (d) hydrolyzing the (N-acetyl)-bis-(aminophenyl)ether with aqueous mineral acid under acid hydrolysis conditions to form an acidic aqueous dispersion of the bis-(aminophenyl)ether product, and (e) recovering said bis-(aminophenyl)ether product from said aqueous dispersion.

2. The process of claim 1 wherein said aminophenate is potassium (N-acetyl)4-aminophenate.

3. The process of claim 1 wherein said halonitrobenzene is p-chloronitrobenzene.

4. The process of claim 1 wherein step (e) includes adding a basic pH adjusting agent to said dispersion in an amount sufficient to adjust the pH of the dispersion to from about 3 pH to about 10 pH.

5. The process of claim 1 wherein said alcoholic solvent is methanol.

6. The process of claim 1 which further includes contacting the reaction mixture with activated carbon during the hydrolysis step.

7. The process of claim 1 wherein said dipolar aprotic solvent is selected from the group consisting of dimethylformamide and dimethylacetamide.

8. The process of claim 1 wherein the separation step includes precipitation of said N-acetyl-aminophenyl-nitrophenyl ether by adding a precipitation-effective amount of water to said reaction mixture.

9. The process of claim 1 wherein said mineral acid is hydrochloric acid.

10. A process for preparing a high-purity substantially colorless 4,4'-oxydianiline product which comprises (a) refluxing a mixture comprising approximately equimolar amounts of (i) (N-acetyl)p-aminophenol, (ii) p-halonitrobenzene, and (iii) potassium or sodium carbonate in a liquid medium comprising a dipolar aprotic solvent, thereby forming N-acetyl-4-aminophenyl-4'-nitrophenyl ether, (b) recovering said ether and forming a dispersion thereof in a lower aliphatic alcoholic solvent therefor, (c) hydrogenating the nitro group of said ether in said dispersion under nitro-group hydrogenation-reduction conditions in the presence of a catalyst to form N-acetylbis(aminophenyl)ether, (d) hydrolyzing said N-acetylbis(aminophenyl)ether with aqueous mineral acid under acid hydrolysis conditions to form an acidic aqueous dispersion of the 4,4'-oxydianiline product, and (e) recovering the 4,4'-oxydianiline product from said aqueous dispersion.

11. The process of claim 10 wherein said p-halonitrobenzene is p-chloronitrobenzene.

12. The process of claim 10 wherein said alcholic solvent is methanol.

13. The process of claim 10 which further includes contacting the reaction mixture with activated carbon during the hydrolysis step.

14. The process of claim 1 wherein said dipolar aprotic solvent is dimethylformamide.

15. The process of claim 10 wherein said dipolar aprotic solvent is selected from the group consisting of dimethylformamide and dimethylacetamide.

16. The process of claim 15 wherein said solvent is dimethylformamide.

* * * * *